United States Patent [19]

Ikejiri et al.

[11] Patent Number: 5,001,453
[45] Date of Patent: Mar. 19, 1991

[54] HUMIDITY SENSOR

[75] Inventors: Masahisa Ikejiri; Michio Yanagisawa, both of Nagano, Japan

[73] Assignee: Seiko Epson Corporation, Tokyo, Japan

[21] Appl. No.: 370,725

[22] Filed: Jun. 23, 1989

[30] Foreign Application Priority Data

Jun. 27, 1988 [JP] Japan ............................... 63-158788
Jul. 18, 1988 [JP] Japan ............................... 63-178587
Jul. 18, 1988 [JP] Japan ............................... 63-178588
Sep. 27, 1988 [JP] Japan ............................... 63-241621

[51] Int. Cl.$^5$ ............................................. H01C 7/00
[52] U.S. Cl. ............................................. 338/35
[58] Field of Search .................. 338/34, 35; 73/336.5; 357/52

[56] References Cited

U.S. PATENT DOCUMENTS

| 4,057,823 | 11/1977 | Burkhardt et al. | 357/52 |
| 4,621,249 | 11/1986 | Uchikawa et al. | 338/35 |
| 4,673,910 | 6/1987 | Uchikawa et al. | 338/35 |
| 4,768,012 | 8/1988 | Williams et al. | 338/34 |
| 4,876,890 | 10/1989 | Mercer et al. | 73/336.5 |

FOREIGN PATENT DOCUMENTS

| 0090048 | 10/1983 | European Pat. Off. . |
| 58-22948 | 2/1983 | Japan . |
| 58-72047 | 4/1983 | Japan . |
| 58-129240 | 8/1983 | Japan . |
| 1593894 | 7/1981 | United Kingdom . |

Primary Examiner—Bruce A. Reynolds
Assistant Examiner—Marvin M. Lateef
Attorney, Agent, or Firm—Blum Kaplan

[57] ABSTRACT

A humidity sensor including an insulating substrate, a pair of electrodes formed on the insulating substrate, and a porous silica film with carbon particles dispersed therein is formed over the insulating substrate and electrodes. A silica film may be formed over the porous silica film or directly on the porous silica film containing carbon particles, or directly on the insulating substrate with the electrodes formed thereon to increase adhesion between the porous silica film and the substrate.

27 Claims, 6 Drawing Sheets

HUMIDITY SENSOR

BACKGROUND OF THE INVENTION

This invention relates to a humidity sensing device and more particularly to a humidity sensor which detects humidity by measuring the change in the electrical characteristic of an element corresponding to the ambient humidity.

Fields requiring humidity measurement and humidity control have been increasing recently and the importance of a humidity sensor is widely recognized. There are several types of humidity sensors which detect humidity by measuring the change in the electrical characteristic of an element corresponding to the ambient humidity, including electrolytic, metallic, polymeric and ceramic humidity sensors. These humidity sensors have each been extensively studied and polymeric and ceramic humidity sensors have been put to practical use. Each of these sensors measures the humidity level by measuring the change in the resistance of an element or the change in the electrostatic capacity of an element as the element absorbs or releases moisture. A resistance-change type humidity sensor is a humidity sensor which detects humidity by measuring the change in the resistance of an element corresponding to the ambient humidity. A capacitance-change type humidity sensor is a humidity sensor which detects humidity by measuring the change in the electrostatic capacity of an element corresponding to the ambient humidity.

Many of the conventional resistance-change type humidity sensors have such high resistance at low humidity that it is difficult to measure low humidity with high accuracy. In order to construct a humidity sensor which is able to measure low humidity with high accuracy, high quality circuitry and a highly accurate mounting technique are required, leading to an increase in manufacturing cost.

Generally, in a resistance-change type humidity sensor, the logarithm of resistance changes linearly with respect to the change in relative humidity. If the linearity is good, a logarithm amplifier is capable of compensating the linearity. In conventional humidity sensors, however, the linearity is poor. Thus, a complicated linearity compensation circuit is required to produce a highly accurate hygrometer.

Generally, in a resistance-change type humidity sensor, the greater the rate of change in the resistance between low humidity and high humidity, the greater the sensitivity. However, when a hygrometer is produced it is difficult to provide the dynamic range of the measuring circuit if the rate of change in the resistance between low humidity and high humidity is too large. Thus, the desirable rate of change in the resistance at a relative humidity of 0 to 100% is about 1 to 3 figures. In conventional humidity sensors, however, the rate of change is large, and in order to produce a highly accurate hygrometer, high quality circuitry and a highly accurate mounting technique are required.

In a capacitance-change type humidity sensor, the linearity of change in electrostatic capacity with respect to relative humidity is poor. Thus, a complicated linearity compensation circuit is required to produce a highly accurate hygrometer. In addition, many capacitance-change type humidity sensors have poor stability at high humidity. Consequently, it is difficult to measure high humidity with high accuracy.

In conventional humidity sensors moisture sensitivity is highly dependent on the temperature and a temperature compensation circuit is required. When temperature dependence is represented by a simple function, it is not necessary to have a complicated temperature compensation circuit. However, in conventional humidity sensors dependence of moisture sensitivity on temperature is not represented by a simple function and a complicated temperature compensation circuit is required to produce a highly accurate hygrometer. Although a complicated temperature compensation circuit may be provided, complete temperature compensation is difficult in a place in which the change in temperature is large. This is due to a difference in thermal response between the humidity sensor and the temperature sensor, or a difference in the location of the temperature sensor and the humidity sensor. In other words, as long as moisture sensitivity of the humidity sensor is dependent on the temperature, accurate humidity measurement remains difficult.

As the prior art illustrates, a highly accurate hygrometer is difficult to produce. A conventional humidity sensor is expensive to manufacture since it requires high quality circuitry and a highly accurate mounting technique. Additionally, inspection and control of the humidity sensor require a large amount of time. In addition, the circuit demands a large volume of power. In view of this, it has not been possible to produce a long life humidity sensor powered by a battery.

With many polymeric humidity sensors, the reliability deteriorates at high temperature and high humidity. The deterioration is especially prominent when an organic solvent is used. Some ceramic humidity sensors have a heating refreshment mechanism to reverse the deterioration by heating an element several hundred degrees (between about 300° and 800° C.) for a determined period. The heating refreshment mechanism can reduce a change in the characteristic with time. This type of humidity sensor, however, cannot be used in an environment in which a combustible gas or dust exists, because there is a danger of explosion or fire when the element is heated to a high temperature. Accordingly, it is not an exaggeration to say that there is no satisfactory humidity sensor in the prior art.

Accordingly, it is desirable to provide an improved humidity sensor which eliminates these problems associated with prior art devices and accurately measures humidity even in a severe environment.

SUMMARY OF THE INVENTION

Generally speaking, in accordance with the invention, an improved humidity sensor which measures the humidity level by measuring the change in the resistance of an element is provided. The humidity sensor includes a pair of electrodes spaced apart on an insulating substrate, and a porous silica film with carbon particles dispersed throughout formed across the substrate and electrodes. In another embodiment a silica film is disposed on the surface of the porous silica film. A silica film may also be disposed on the insulating substrate with the electrodes provided on the silica film. In another further embodiment a silica film is disposed on the substrate with the electrodes thereon, the porous silica film disposed over the electrodes and a silica film on the porous silica film.

Accordingly, it is an object of this invention to provide an improved humidity sensor capable of measuring humidity in a highly accurate manner.

Another object of the invention is to provide an improved humidity sensor having good linear correlation between the logarithm of the resistance and the change in relative humidity.

A further object of the invention is to provide a improved humidity sensor which does not require a complicated temperature compensation circuit.

A still further object of this invention is to provide an improved humidity sensor which does not require a complicated linear compensation circuit.

Still other objects and advantages of the invention will in part be obvious and will in part be apparent from the specification.

The invention accordingly comprises the art of possessing the features, properties and the relation of elements and the several steps and the relation of one or more of such steps with respect to each of the others, which are exemplified in the following detailed disclosure, and the scope of the invention will be indicated in the claims.

DESCRIPTION OF THE DRAWINGS

For a fuller understanding of the invention, reference is had to the following description taken in connection with the accompanying drawings, in which.

DESCRIPTION OF THE PREFERRED EMBODIMENTS

Figure 1:
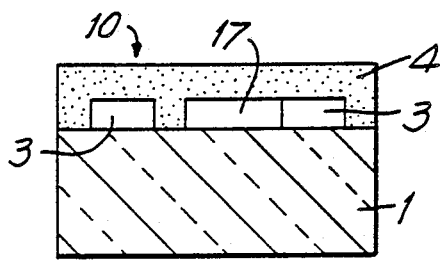
FIG. 1 is a sectional view of a humidity sensor constructed and arranged in accordance with the invention.
Figure 5:
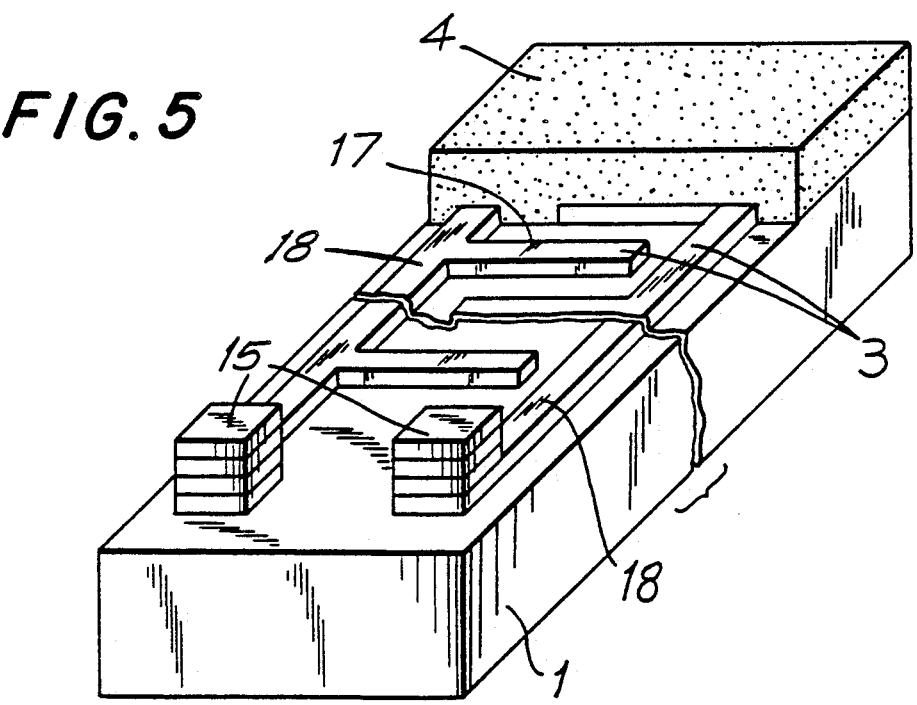
FIG. 5 is a sectional view of the humidity sensor of FIG. 1.
Figure 6:
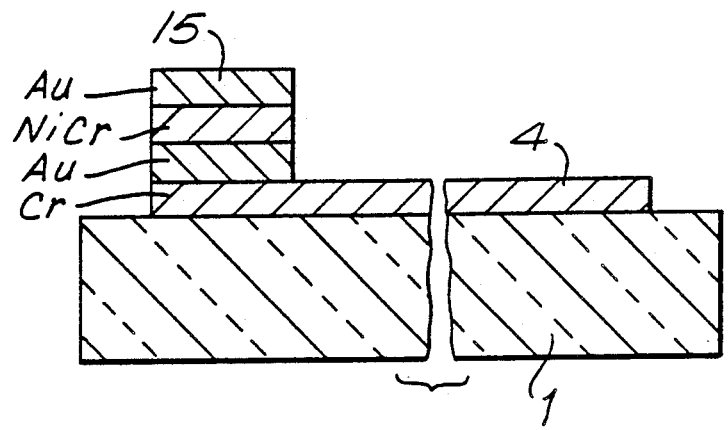
FIG. 6 is a sectional view of the humidity sensor of FIG. 1.
Figure 7:
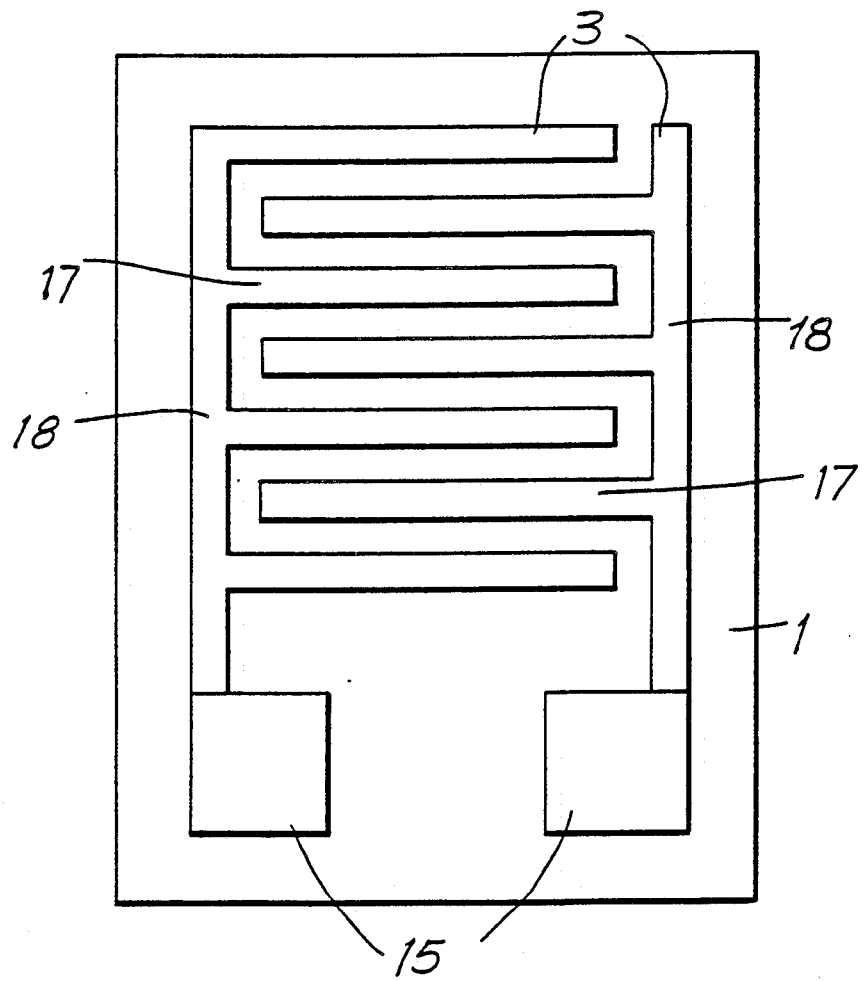
FIG. 7 is a plan view of a pair of electrodes of the humidity sensor of FIG. 1.

A humidity sensor 10 constructed in accordance with the invention is shown in cross-section in FIG. 1 and in a cut-away perspective in FIG. 5. Humidity sensor 10 includes an insulating substrate and a pair of electrodes 3 provided on insulating substrate 1. A porous silica film 4 containing carbon particles is disposed over insulating substrate 1 and electrodes 3.

Insulating substrate is formed of an insulating material. Preferably, it is an alumina substrate, a glass substrate or a refractory brick substrate in terms of reliability and the ability to mass produce the humidity sensor. When particularly high reliability is required of a humidity sensor having a glass substrate, silica glass may be used.

Electrodes 3 are formed in the shape of comb electrodes, each of which has a base member 18 and teeth 17 like that of a comb, in order to reduce the resistance of humidity sensor 10. Teeth 17 are interlaced in alternating fashion. Electrodes 3 are formed of a metal selected from the group consisting of Au, Ag, Pt, Pd and Cr, an alloy containing at least one element selected therefrom, or $RuO_2$. Adhesion between insulating substrate 1 or silica film 22 in FIG. 14 and electrodes 3 may be improved when electrodes 3 are formed in a multi-layer structure. This multilayer structure is formed by depositing a Cr electrode layer on insulating substrate 1 or silica film 22 formed on insulating substrate 1 and then depositing an Au electrode layer on the Cr electrode layer.

If a chromium comb electrode is used at least in the portion where porous silica film 4 containing carbon particles is formed, it is possible to improve the adhesion between electrodes 3 and porous silica film 4 containing carbon particles. In addition, the connection of a lead wire is facilitated and the reliability is improved if a multi-layered electrode is used. Such a multilayer electrode may include at least one layer of a metal selected from the group consisting of Au, Ag, Pt, Pd and Cr or an alloy containing at least one element selected therefrom on the Cr electrode layer at the terminal portion 15 where the lead wire is connected.

By varying the content of the carbon particles dispersed in the porous silica film or the thickness of the porous silica film, conductivity varies freely. Thus, the linearity of the change in resistance with respect to the change in relative humidity improves. It is possible to measure a wide range of humidity levels with high accuracy since it is easy to measure low humidity, which increases the resistance of a humidity sensor.

The relationship between relative humidity and the logarithm of the resistance is linear in a conventional resistancechange type humidity sensor. In a humidity sensor constructed in accordance with the invention, it is also possible to maintain the linear relationship between the relative humidity and the resistance by controlling the carbon particle content and the thickness of the porous silica film containing carbon particles. This permits dispensing with the need for a logarithm amplifier. In addition, since dependence of moisture sensitivity on temperature is low, a temperature compensation circuit is not necessary. The characteristics of the humidity sensor do not deteriorate even in severe environments since the carbon particles and the silica film are chemically stable. Thus, a humidity sensor prepared i accordance with the invention is highly accurate and highly reliable.

The content of carbon particles in porous silica film 4 is between about 10 and 50 weight percent, and preferably between about 15 and 45 weight percent If the content of the carbon particles is less than about 10 weight percent, the resistance becomes very high. On the other hand, if the content of carbon particles exceeds about 50 weight percent, the sensitivity becomes very low.

The thickness of the porous silica film including the carbon particles is between about 1 and 300 $\mu$m, and preferably between about 5 and 250 $\mu$m. If the thickness is less than about 1 $\mu$m, the resistance becomes very high. On the other hand, if the thickness exceeds about 300 $\mu$m, the sensitivity becomes very low.

The porous silica film containing carbon particles is easily formed First, a silica sol with carbon particles dispersed throughout is formed by dispersing silica particles and carbon particles in a hydrolyzed solution of silicon alkoxide. The silica particles and the carbon particles may be dispersed either before or after hydrolysis of the silicon alkoxide. The sol is formed into a film and the resulting film is heat treated to form the porous silica film containing carbon particles. Thus, the carbon particle content is easily controlled by the amount of carbon particles dispersed in the silica sol.

The sol gel which includes synthesizing a ceramic material from a liquid phase of a metal alkoxide can produce the ceramic material at a lower temperature than conventional methods. It is possible in accordance with the invention to produce a silica film or a porous silica film containing carbon particles at a temperature of not higher than about 500° C, which is much lower than with conventional methods. In addition, a sol gel method can produce a ceramic composite which is not produced by conventional methods. Accordingly, the manufacturing cost is reduced, thus enabling the low cost manufacture of a humidity sensor. In addition, the production of a composite of silica and carbon, which is difficult by conventional methods, is facilitated in accordance with the invention.

When the above described sol is formed into a film, a dip coating, spin coating, roll coating or screen printing method is performed depending on the viscosity of the sol and the required film thickness.

The silica film formed on the insulating substrate improves the adhesion between the insulating substrate and the porous silica film containing carbon particles. The silica film formed on the porous silica film containing carbon particles and functions as a protective film for the porous silica film having carbon particles thus enhancing the mechanical strength of the porous silica film containing carbon particles and improving the durability and the reliability of the humidity sensor.

As described above, since it is easy to manufacture a humidity sensor in accordance with the invention, the humidity sensor is easily mass produced. The manufacturing cost is also low due to the low cost of the raw materials and it is possible to produce an inexpensive humidity sensor. Thus, in accordance with the invention, it is possible to mass produce a highly accurate and reliable humidity sensor.

The invention will be better understood with reference to the following examples. The examples are presented for purposes of illustration only and are not intended to be construed in a limiting sense.

EXAMPLE 1

Comb electrodes were formed on an alumina substrate by sputtering Cr. Next, Au, NiCr and Au were sputtered, in that order, on the comb electrodes at the portions to which lead wires were connected. That is, the comb electrodes solely of Cr were located at the portions at which a porous silica film with carbon particles dispersed therein was formed and the four-layered electrodes of Cr, Au, NiCr and Au in that order from the substrate were located at the portions of the electrode where lead wires were connected.

Tetraethoxysilane ($Si(OC_2H_5)_4$) was hydrolyzed by adding 25 ml of ethanol and 4 ml of 0.02 N hydrochloric acid to 50 ml of tetraethoxysilane and the mixture was stirred for 1 hour. 10 ml of glycerin and 13.5 g of fine silica powder were added to the hydrolyzed mixture and the resultant mixture was stirred for 30 minutes. Next, 5.4 g of activated carbon and 2.7 g of carbon black were added to the resultant mixture and the mixture was stirred for 30 minutes to produce a silica sol with carbon particles dispersed therein. The alumina substrate with electrodes thereon was dip coated in the silica sol, dried at 100° C. for 10 minutes and sinter ®d at 430° C. for 30 minutes, to form a porous silica film with carbon particles dispersed throughout. The content of the carbon particles in the porous silica film was 23 weight percent and the thickness of the porous silica film was 15 $\mu$m.

Figure 2:
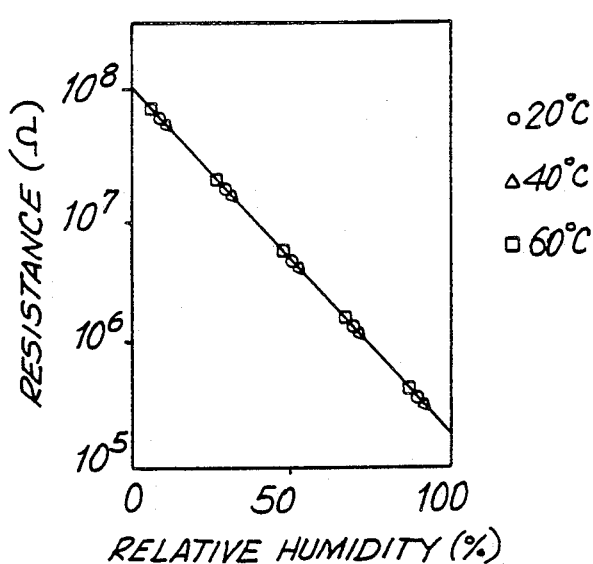
FIG. 2 is a graph showing the relationship between relative humidity and resistance for the humidity sensor of FIG. 1.
Figure 3:
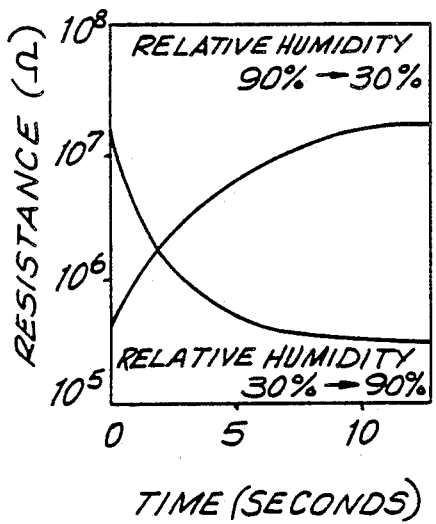
FIG. 3 illustrates the response curve of the humidity sensor of FIG. 1.

The humidity sensor prepared is as shown in FIGS. 1 and 4–7. The moisture sensitivity of humidity sensor 10 is shown in FIG. 2. FIG. 2 shows that the linearity of the logarithm of resistance with respect to relative humidity is good. Since the resistance is easy to measure even at a low humidity, a complicated linearity compensation circuit and a high resistance measuring circuit are not necessary Since the temperature dependence of the moisture sensitivity is small, the humidity sensor does not require a temperature compensation circuit The response characteristic of humidity sensor 10 is shown in FIG. 3. It is evident from FIG. 3 that the humidity sensor has a quick response time The moisture sensitivity was measured after the humidity sensor was left to stand in a thermo-hygrostat of a temperature of 60° C. and a relative humidity of 95% for 1,000 hours in order to examine the durability of the reliability of the humidity sensor. The results were the same as in FIG. 2 within the range of errors in measurement. Accordingly, the humidity sensor proved to be highly durable and highly reliable. Thus, it is possible to produce a hygrometer and a low cost humidity detector having simple circuitry, which consumes a low volume of power and which has high accuracy, high-speed responsiveness and high reliability.

Similar humidity sensors were produced by using Ag, Cu, Pt, and Ag-Pt alloy and a Pt-Pd alloy, respectively, in place of Au at the portions of the electrodes where the lead wires were connected.

EXAMPLE 2

Figure 8:
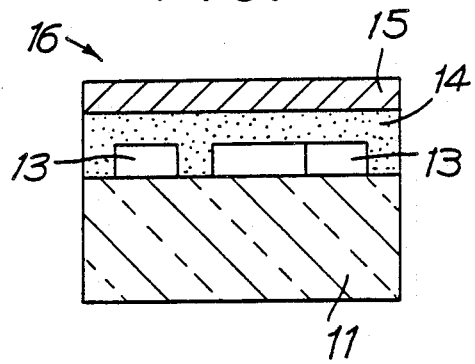
FIG. 8 is a sectional view of a humidity sensor constructed in accordance with another embodiment of the invention.
Figure 4:
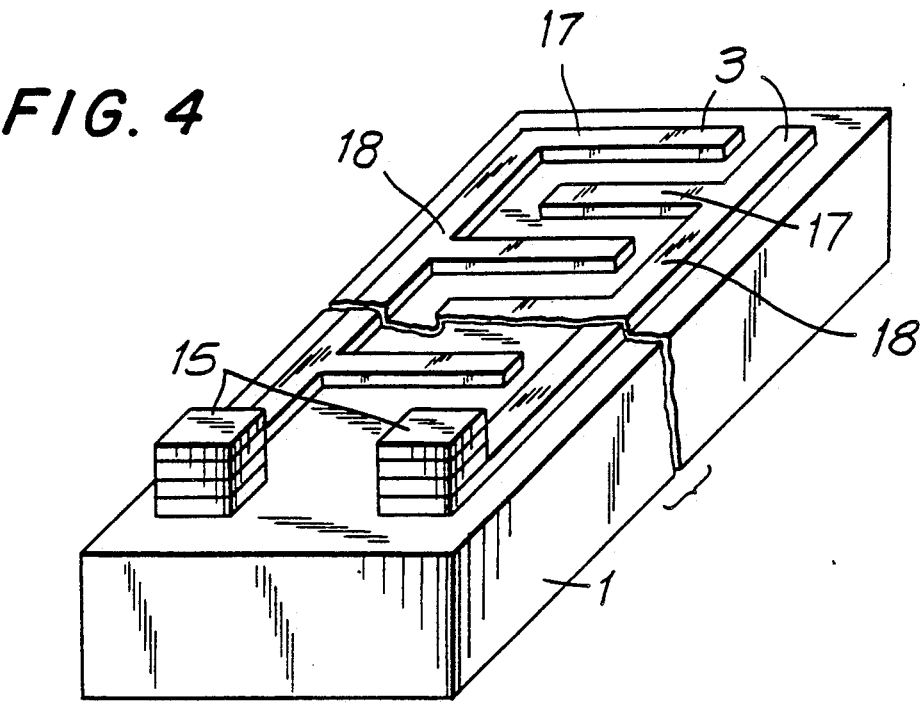
FIG. 4 is a perspective view of a pair of comb electrodes of the humidity sensor of FIG. 1.

A humidity sensor prepared in accordance with a second embodiment of the invention is shown in FIG. 8 generally as sensor 16. In this embodiment a silica film 15 formed on a porous silica film 14. The remaining elements of humidity sensor 16 are similar to the embodiment of FIG. 1 and include an insulating substrate 11, a pair of electrodes 13 provided on insulating substrate 11 and porous silica film 14 containing carbon particles formed over the exposed portions of insulating substrate 11 and electrodes 13. A humidity sensor having the structure shown in FIG. 8 was prepared as follows. Tetraethoxysilane was hydrolyzed by adding 35 ml or ethanol and 16 ml of 0.02 N hydrochloric acid to 50 ml or tetraethoxysilane and the mixture was stirred for 1 hour. Next, 20 ml of ethylene glycol, 5 g of activated carbon and 9.5 g of carbon black were added to the mixture and the resultant mixture was stirred for 30 minutes. Then 20 g of fine silica powder was added, and the mixture containing silica powder was stirred for 30 minutes to produce a silica sol with carbon particles dispersed throughout.

An alumina substrate with Pt-Pd comb electrodes formed thereon by screen printing was spin coated with the silica sol, dried at 150° C. for 1 hour and sintered at 380° C. for 1 hour to form a porous silica film with carbon particles dispersed throughout. The content of the carbon particles in the porous silica film was 30 wt% and the thickness of the porous silica film was 30 μm.

Tetraethoxysilane was hydrolyzed by adding 35 ml of ethanol and 4 ml of 0.02 N hydrochloric acid to 50 ml of tetraethoxysilane and the mixture was stirred for 1 hour. 10 g of fine silica powder was added thereto and the mixture was stirred for 30 minutes to obtain a silica sol. The silica sol was spin coated onto the porous silica film having carbon particles dispersed throughout, dried at 120° C. for 30 minutes and sintered at 400° C. for 20 minutes, to produce a silica film across the upper surface of the porous silica film.

The respective humidity sensor is shown in FIG. 8.

Figure 9:
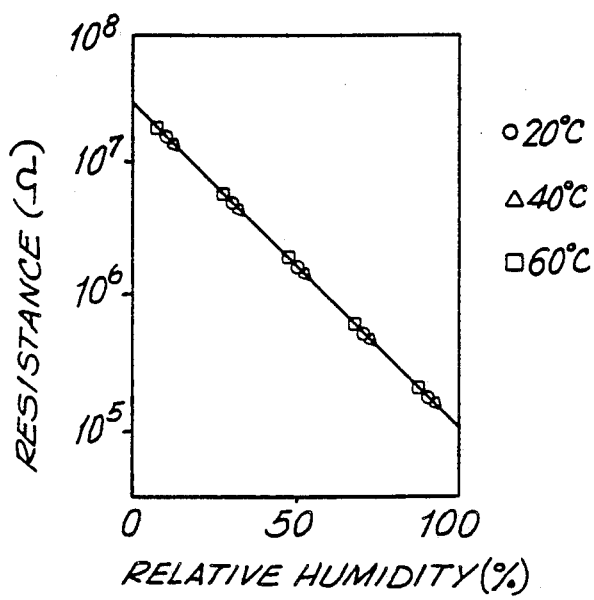
FIG. 9 is a graph illustrating the logarithmic relationship between relative humidity and resistance of the humidity sensor of FIG. 8.
Figure 10:
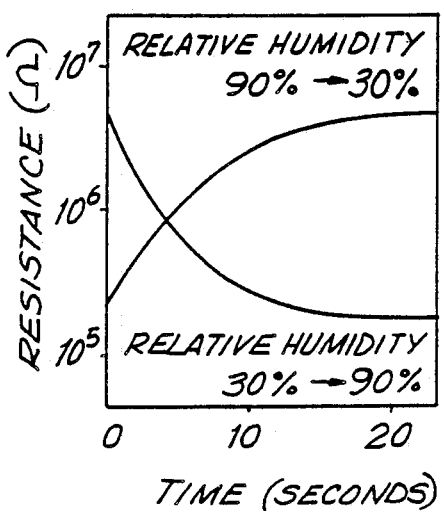
FIG. 10 is a response curve of the humidity sensor of FIG. 8.

The moisture sensitivity of the humidity sensor is shown in FIG. 9. The linearity of the logarithm of resistance with respect to relative humidity is good. A complicated linearity compensation circuit and a high resistance measuring circuit are not necessary since the resistance is easy to measure even at a low humidity. A temperature compensation circuit is also not required, since the temperature dependence on moisture sensitivity is small The humidity sensor is quick to respond as shown by the response characteristic in FIG. 10. The durability and the reliability o the humidity sensor was examined by measuring the moisture sensitivity after the humidity sensor was left to stand in a atmosphere saturated with water and ethanol steam at 60° C. for 1,000 hours. The results were substantially the same as in FIG. 9, within the range of errors in measurement. Accordingly, the humidity sensor proved to be reliable even in a very severe environment.

A similar humidity sensor was produced by using Pt as the material for the comb electrode in place of a Pt-Pd alloy.

EXAMPLE 3

A humidity sensor having the structure shown in FIG. 8 was prepared a follows. Tetraethoxysilane was hydrolyzed by adding 50 ml of ethanol, 8 ml of 0.02 N hydrochloric acid and 10 g of fine silica powder to 50 ml of tetraethoxysilane and the mixture was stirred for 1 hour. Next, 5 ml of monoolein and 18 g of activated carbon were added to the mixture and the mixture was stirred for 30 minutes to produce a silica sol with carbon particles dispersed throughout.

Comb electrodes formed of $RuO_2$ were screen printed on a refractory brick substrate. The substrate, including the $RuO_2$ comb electrodes, was roll coated with the silica sol, dried at 60° C. for 24 hours and sintered at 450° C. for 20 minutes to form a porous silica film containing carbon particles on the substrate astride the electrodes. The content of the carbon particles in the porous silica film was 43 wt% and the thickness of the porous silica film was 250 μm.

Tetraethoxysilane was then hydrolyzed by adding 50 ml of ethanol, 8 ml of 0.02 N hydrochloric acid and 20 g of fine silica powder to 50 ml of tetraethoxysilane and the mixture was stirred for 1 hour, to produce a silica sol. The porous silica film with carbon particles dispersed throughout was roll coated with the silica sol, dried at 80° C. for 5 hours and sintered at 480° C. for 10 minutes to produce a silica film. The resulting humidity sensor is as shown in FIG. 8.

Figure 11:
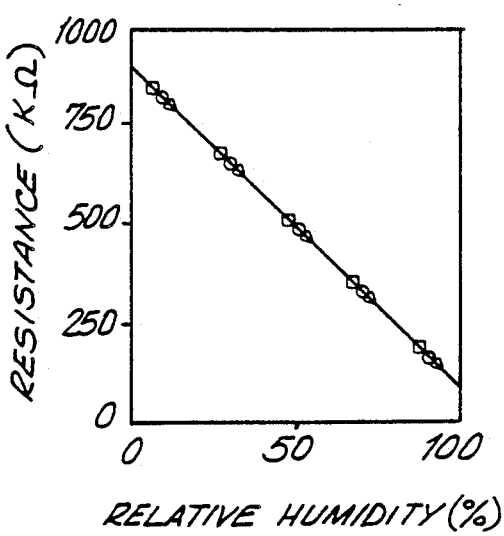
FIG. 11 is a graph illustrating the relationship between relative humidity and resistance of another humidity sensor having the structure shown in FIG. 8.

FIG. 11 illustrates the moisture sensitivity of the humidity sensor. It is evident from FIG. 11 that there is a linear relationship between relative humidity and resistance. Accordingly, the humidity sensor is able to measure humidity with high accuracy with a simple circuit and a logarithm amplifier is not necessary. Thus, it is possible to produce a humidity sensor having a linear relationship between relative humidity and resistance by controlling the content of the carbon particles and the thickness of the porous silica film.

The durability and the reliability of the humidity sensor was examined by measuring the moisture sensitivity after the humidity sensor was placed in boiling water for 1 hour and dried at 100° C. for 1 hour. The results were the same as in FIG. 11, within the range of errors in measurement. Accordingly, the humidity sensor proved to be stable even in a very severe environment.

EXAMPLE 4

Figure 12:
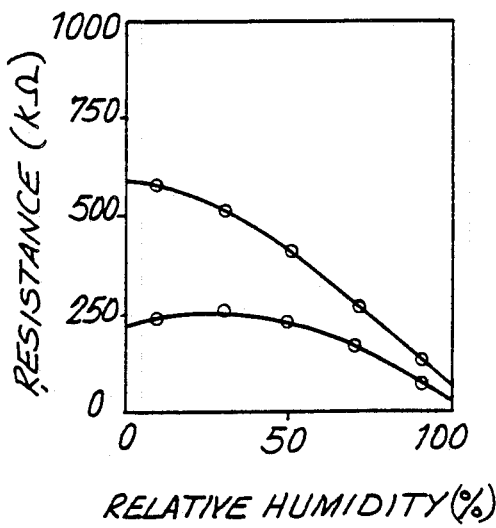
FIG. 12 is a graph illustrating the relationship between relative humidity and resistance of a humidity sensor having the structure shown in FIG. 8.

Humidity sensors were prepared in the same manner as in Example 3, except that the amount of activated carbon used was 22 g and 25 g, respectively. The content of carbon particles in the porous silica film were 48 wt % and 52 wt %, respectively. The moisture sensitivity of the humidity sensors are shown in FIG. 12. In FIG. 12, curve A represents the moisture sensitivity of the humidity sensor in which the carbon particle content of the porous silica film was 48 wt %. Curve B represents the moisture sensitivity of the humidity sensor in which the carbon particle content of the porous silica film was 52 wt %. It is clear from FIG. 12 that when the content of the carbon particles in the porous silica film exceeds 45 wt %, sensitivity is lower at low humidity, and when it exceeds 50 wt %, sensitivity is lower at all humidity levels. Accordingly, a humidity sensor having good characteristics is obtained when the content of the carbon particles in the porous silica film is not more than about 50 wt %, and preferably not more than about 45 wt %.

EXAMPLE 5

Figure 13:
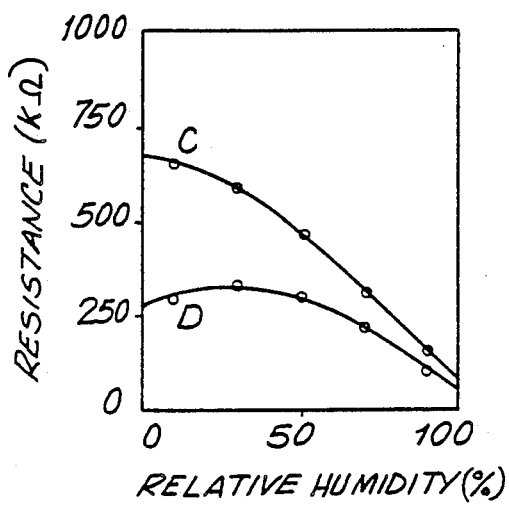
FIG. 13 is a graph illustrating the relationship between relative humidity and resistance of a humidity sensor having the structure shown in FIG. 8.

Humidity sensors were prepared in the same manner as in Example 3, except that the thickness of the porous silica film containing carbon particles was changed to 300 μm and 350 μm, respectively. The moisture sensitivity of the humidity sensors are shown in FIG. 13. In FIG. 13, curve C represents the moisture sensitivity of the humidity sensor in which the porous silica film containing carbon particles was 300 μm thick. Curve D represents the moisture sensitivity of the humidity sensor in which the porous silica film containing carbon particles was 350 μm thick.

It is evident from FIG. 13 that when the thickness of the porous film containing carbon particles exceeds 250 μm, the sensitivity is lowered at low humidity, and when it exceeds 300 μm, the sensitivity is lowered at all humidity levels. Accordingly, a humidity sensor having excellent characteristics is obtained when the thickness of the porous film containing carbon particles is not more than about 300 μm, and more preferably not more than about 250 μm.

EXAMPLE 6

Figure 14:
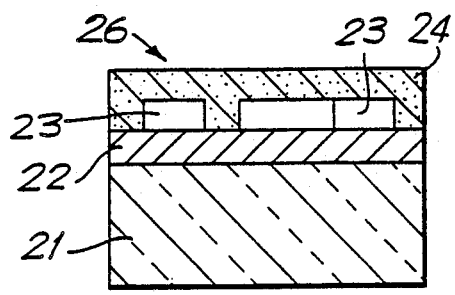
FIG. 14 is a sectional view of a humidity sensor constructed in accordance with a further embodiment of the invention.

A humidity sensor having the structure as a humidity sensor 26 in FIG. 14 which includes an insulating substrate 21, a silica film 22 formed on insulating substrate 21, a pair of electrodes 23 formed on silica film 22, and a porous silica film 24 containing carbon particles formed over the exposed surface silica film 22 and electrodes 23.

Tetraethoxysilane was hydrolyzed by adding 40 ml of 0.02 N hydrochloric acid and 25 g of fine silica powder to 50 ml of tetraethoxysilane and the mixture was stirred for 1 hour to produce a silica sol. The silica sol was screen printed on a glass substrate and sintered at 300° C. for 1 hour, to form a silica film Cr was deposited on the silica film and Au was deposited on the Cr to form comb electrodes.

Figure 15:
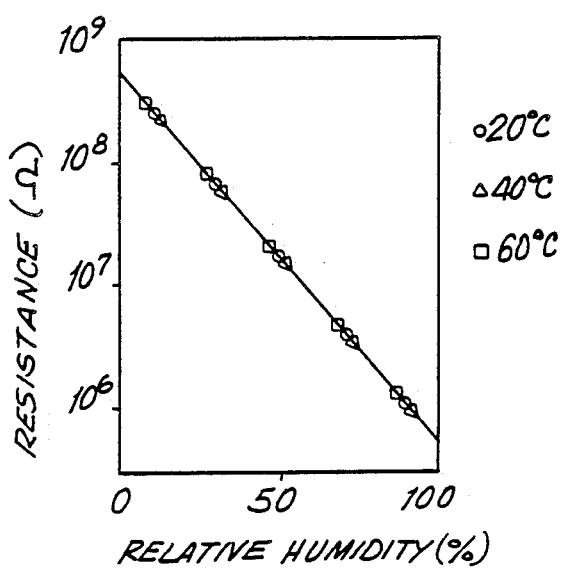
FIG. 15 is a graph illustrating the relationship between relative humidity and resistance of the humidity sensor shown in FIG. 14.

Tetraethoxysilane was next hydrolyzed by adding 50 ml of 0.02 N hydrochloric acid, 25 g of fine silica powder and 7.3 g of carbon black to 50 ml of tetraethoxysilane and the mixture was stirred for 1 hour to form a silica sol containing carbon particles dispersed throughout. The silica sol was screen printed on the glass substrate having the silica film and the comb electrodes and the silica sol was sintered at 350° C. for 10 hours to form a porous silica film containing carbon particles. The resulting structure is as shown in FIG. 14. The content of the carbon particles in the porous silica film was 16 wt % and the thickness of the porous silica film was 5 μm. The moisture sensitivity of the humidity sensor is shown in FIG. 15.

EXAMPLE 7

Figure 16:
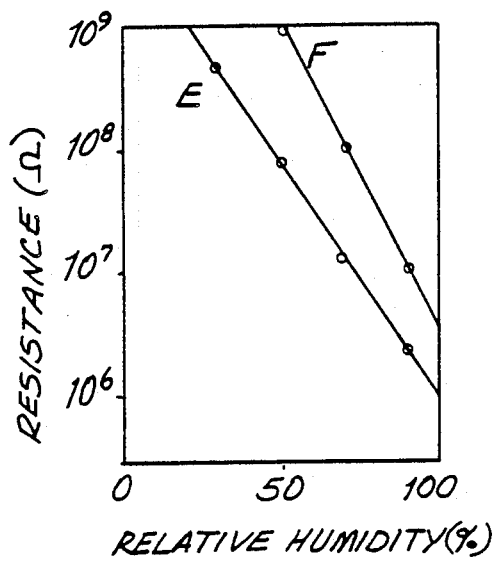
FIG. 16 is a graph illustrating the relationship between relative humidity and resistance of a humidity sensor having the structure shown in FIG. 14.

Humidity sensors were prepared in the same manner as Example 6, except that the amount of carbon black was 5.3 g and 3.3 g, respectively. The content of carbon particles in the porous silica film was 12 wt % and 8 wt %, respectively. The moisture sensitivity of the humidity sensors are shown in FIG. 16. In FIG. 16, curve E represents the moisture sensitivity of the humidity sensor having a carbon particle content in the porous silica film of 12 wt %. Curve F represents the moisture sensitivity of the humidity sensor having a carbon particle content in the porous silica film of 8 wt %.

It is clear from FIG. 16 that when the carbon particle content in the porous silica film is less than about 15 wt%, the resistance becomes high at low humidity, and when the carbon particle content is less than about 10 wt%, the resistance becomes very high. Accordingly, a humidity sensor having good characteristics is obtained when the carbon particle content in the porous silica film is not less than about 10 wt %, and preferably not less than about 15 wt %.

EXAMPLE 8

Figure 17:
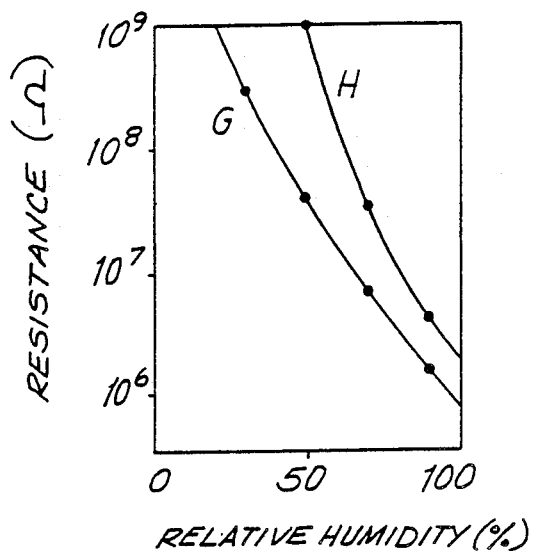
FIG. 17 is a graph illustrating the relationship between relative humidity and resistance of a humidity sensor having the structure shown in FIG. 14.

Humidity sensors were prepared in the same manner as in Example 6, except that the thickness of the porous silica film containing carbon particles was changed to 1 μm and 0.5 μm, respectively. The moisture sensitivity of the humidity sensors are shown in FIG. 17. In FIG. 17, curve G represents the moisture sensitivity of the humidity sensor in which the thickness of the porous film containing carbon particles was 1 μm. Curve H represents the moisture sensitivity of the humidity sensor in which the thickness of the porous film containing carbon particles was 0.5 μm.

FIG. 17 shows that when the thickness of the porous film containing carbon particles is less than about 5 μm, the resistance becomes high at low humidity, and when the thickness is less than about 1 μm, the resistance becomes very high. Accordingly, a humidity sensor having good characteristics is obtained when the thickness of the porous film containing carbon particles is not less than about 1 μm, and preferably not less than about 5 μm.

EXAMPLE 9

Figure 18:
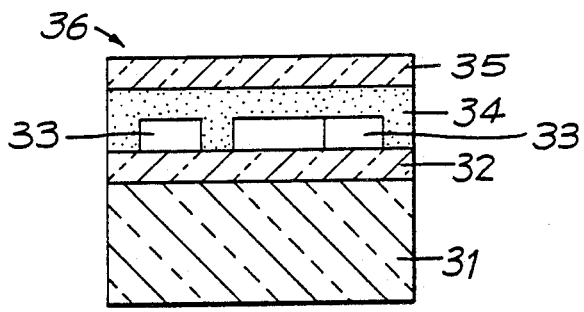
FIG. 18 is a sectional view of a humidity sensor constructed in accordance with yet another embodiment of the invention.

A humidity sensor having the structure shown in FIG. 18 was prepared as follows. A humidity sensor 36 includes an insulating substrate 31, a silica film 32 formed on insulating substrate 31, a pair of electrodes 33 formed on silica film 32, a porous silica film 34 containing carbon particles formed on the exposed surface of silica film 32 and electrodes 33 and a silica film 35 formed on porous silica film 34 containing carbon particles.

Tetraethoxysilane was hydrolyzed by adding 25 ml of ethanol, 16 ml of 0.02 N hydrochloric acid and 13.5 g of fine silica powder to 50 ml of tetraethoxysilane and the mixture was stirred for 1 hour to form a silica sol designated "A". A silica glass substrate was dip coated with silica sol A, dried at 50° C. for 10 minutes and sintered at 500° C. for 30 minutes, to form a silica film. Comb electrodes of an Ag-Pd alloy were screen printed on the silica film.

Tetraethoxysilane was hydrolyzed by adding 15 ml of ethanol, 2 ml of 0.02 N hydrochloric acid, 8.7 g of activated carbon and 8.7 of carbon black to 50 ml of tetraethoxysilane and the moisture was stirred for 1 hour. 50 ml of polyethylene glycol and 15 g of fine silica powder were added thereto and the resultant mixture was stirred for 30 minutes to form a silica sol (silica sol "B") containing carbon particles. The silica glass substrate having the silica film and the comb electrodes was dip coated with silica sol B, dried at 200° C. for 5 minutes and sintered at 400° C. for 1 hour to form a porous silica film containing carbon particles dispersed throughout. The carbon particles content of the porous silica film was 38 wt % and the thickness of the porous silica film was 100 μm.

The porous silica film containing carbon particles was dip coated with silica sol A, dried at 50° C. for 10 minutes and sintered at 380° C. for 5 hours to form a silica film. The humidity sensor formed is shown in FIG. 18.

Figure 19:
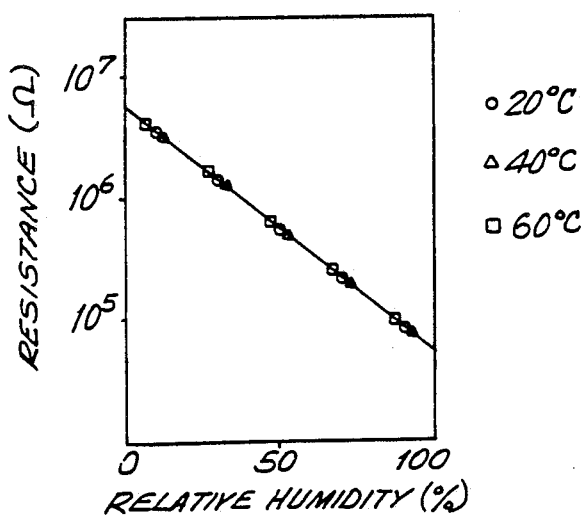
FIG. 19 is a graph illustrating the relationship between relative humidity and resistance of the humidity sensor of FIG. 18.

FIG. 19 shows the moisture sensitivity of the humidity sensor. The results in FIG. 19 show that the linearity of the logarithm of resistance with respect to relative humidity is good, and the humidity sensor is highly accurate since the resistance is easy to measure even at low humidity. The durability and the reliability of the humidity sensor was tested by measuring the moisture sensitivity after the humidity sensor was washed with ultrasonic waves in acetone for 10 minutes The results were the same as in FIG. 19, with the range of errors in measurement. Accordingly, the characteristics of the humidity sensor proved to be stable even in a very severe environment.

A similar humidity sensor was produced by substituting Ag for the Ag-Pd alloy as the material for the comb electrodes.

In summary, since the humidity sensor prepared in accordance with the invention includes an insulating substrate, a pair of electrodes formed on the insulating substrate, and a porous silica film containing carbon particles, it is possible to vary the conductivity freely by controlling the carbon particles content of the porous silica film.

Thus, it is possible to produce a humidity sensor which has good linear correlation between the change in resistance and the change in relative humidity. The humidity sensor is capable of accurately measuring a wide range of humidity levels with a simple circuit and the resistance is easy to measure at low humidity when the resistance is high. It is also possible to produce a humidity sensor which does not require a logarithm amplifier, since there is a linear relationship between relative humidity and resistance. In addition, a temperature compensation circuit is not necessary since the moisture sensitivity dependence on temperature is small. Thus, it is possible to use a simplified humidity measuring circuit and to produce a highly accurate humidity measuring device at a low cost which is economical with regard to power consumption.

Even in a severe environment the carbon particles and the silica film do not deteriorate and remain chemically stable. Thus, heat refreshment is not necessary and the humidity sensor can be used in an environment containing combustible gas or dust. Furthermore, since the humidity sensor responds quickly to changes in humidity and the change in the characteristic is small with respect to time, the humidity sensor may be used in a highly accurate humidity control device.

The humidity sensor in accordance with the invention is easily mass produced. Additionally, the manufacturing cost is low since the raw materials are inexpensive.

As described above, a humidity sensor in accordance with the invention is highly accurate and reliable. The humidity sensor is applicable to a wide variety of fields which require humidity measurement and humidity control.

It will thus be seen that the objects set forth above, among those made apparent from the preceding description, are efficiently attained and, since certain changes may be made in carrying out the above method and in the construction set forth without departing from the spirit and scope of the invention, it is intended that all matter contained in the above description and shown in the accompanying drawings shall be interpreted as illustrative and not in a limiting sense.

The invention accordingly comprises the features of construction, combination of elements, and arrangement of parts which will be exemplified in the construction hereinafter set forth, and the scope of the invention will be indicated in the claims.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. A humidity sensor, comprising:
   an insulating substrate;
   a pair of electrodes on said insulating substrate; and
   a porous silica film containing dispersed carbon particles over the exposed surface of said insulating substrate and electrodes.

2. The humidity sensor of claim 1, wherein said insulating substrate is alumina.

3. The humidity sensor of claim 1, wherein said insulating substrate is glass.

4. The humidity sensor of claim 1, wherein said insulating substrate is refractory brick.

5. The humidity sensor of claim 1, wherein said electrodes are comb electrodes formed of a metal selected from the group consisting of Au, Ag, Pt, Pd and Cr, an alloy containing at least one element selected therefrom, or $RuO_2$.

6. The humidity sensor of claim 1, wherein said electrodes are Cr and include a terminal portion for connection to a lead electrode, said terminal portion further including at least one layer of a metal selected from the group consisting of Au, Ag, Pt, Pd and Cr or an alloy containing at least one element selected therefrom on the Cr electrode.

7. The humidity sensor of claim 1, wherein said porous silica film including carbon particles contains between about 10 and 50 wt % of said carbon particles.

8. The humidity sensor of claim 1, wherein said porous silica film including carbon particles contains between about 15 and 45 wt % of said carbon particles.

9. The humidity sensor of claim 1, wherein said porous silica film including carbon particles is between about 1 and 300 μm thick.

10. The humidity sensor of claim 1, wherein said porous silica film containing carbon particles is produced by forming a silica sol including carbon particles into a film and heat treating said film.

11. The humidity sensor of claim 10, wherein said silica sol containing carbon particles is formed by dispersing silica particles and carbon particles in a hydrolyzed solution of silicon alkoxide.

12. A humidity sensor, comprising:
    an insulating substrate;
    a pair of electrodes formed on said insulating substrate;
    a porous silica film including dispersed carbon particles formed on the exposed surface of said insulating substrate and electrodes; and
    a silica film formed on said porous silica film including carbon particles.

13. The humidity sensor of claim 12, wherein said silica film is produced by depositing a silica sol o the substrate and heat treating said film.

14. The humidity sensor of claim 13, wherein said silica sol is formed by dispersing silica particles in a hydrolyzed solution of silicon alkoxide.

15. A humidity sensor, comprising:
    an insulating substrate;
    a silica film formed on said insulating substrate;
    a pair of electrodes formed on said silica film; and a porous silica film including dispersed carbon particles formed on the exposed surface of said silica film and electrodes.

16. A humidity sensor, comprising:
an insulating substrate;
a silica film formed on said insulating substrate;
a pair of electrodes formed on said silica film;
a porous silica film including dispersed carbon particles formed on the exposed surface of said silica film and electrodes; and
a silica film on the upper surface of said porous silica film including carbon particles.

17. A method of preparing a humidity sensor, on an insulating substrate, comprising:
disposing a pair of spaced apart electrodes on the substrate;
depositing a silica sol with carbon particles dispersed therein over the exposed surface of the substrate and electrodes; and
drying the deposited film to form a porous silica film with carbon particles.

18. The method of claim 17, wherein the electrodes are formed by sputtering.

19. The method of claim 17, wherein the porous silica film is formed by dip coating.

20. The method of claim 17, wherein the electrodes are formed by screen printing.

21. The method of claim 17, wherein the porous silica film was deposited by spin coating.

22. The method of claim 17, further including the step of forming a silica film on the porous silica film by depositing a silica sol thereon.

23. The method of claim 22, wherein the silica film is deposited by spin coating.

24. The method of claim 17, wherein the porous silica film was deposited by roll coating a silica sol including dispersed carbon particles.

25. The method of claim 17, further including the step of sintering at a temperature up to about 500° C.

26. The method of claim 17, further including the step of depositing a thin silica film directly o the surface of the substrate and forming the electrodes on the thin silica film.

27. The method of claim 26, further including forming a silica film on the upper surface of the porous silica film.

* * * * *